(12) United States Patent
Tiongson

(10) Patent No.: US 6,368,638 B1
(45) Date of Patent: Apr. 9, 2002

(54) PROCESS OF MAKING AN AQUEOUS CALCIUM CARBONATE SUSPENSION

(75) Inventor: Antonio Tiongson, Neshanic, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/623,710

(22) PCT Filed: Mar. 11, 1999

(86) PCT No.: PCT/US99/04652

§ 371 Date: Sep. 7, 2000

§ 102(e) Date: Sep. 7, 2000

(87) PCT Pub. No.: WO99/45937

PCT Pub. Date: Sep. 16, 1999

Related U.S. Application Data

(60) Provisional application No. 60/077,659, filed on Mar. 11, 1998.

(51) Int. Cl.[7] .................................................. A61K 33/10
(52) U.S. Cl. ........................................ 424/687; 424/468
(58) Field of Search .................................. 424/687, 488

(56) References Cited

U.S. PATENT DOCUMENTS 5,272,137 A * 12/1993 Blase et al. .................... 514/54
6,117,474 A *  9/2000 Kamada et al. ............. 426/590
6,140,376 A * 10/2000 Golley et al. .................. 516/78

* cited by examiner

*Primary Examiner*—James H. Reamer
(74) *Attorney, Agent, or Firm*—Dara L. Dinner; Stephen Venetianer; Charles M. Kinzig

(57) ABSTRACT

The present invention relates to a high dosage calcium carbonate aqueous antacid pharmaceutical suspension for oral use, and methods of preparation.

14 Claims, No Drawings

PROCESS OF MAKING AN AQUEOUS CALCIUM CARBONATE SUSPENSION

This application is the §371 mational stage entry of PCT/US99/04652, filed Mar. 11, 1999 which claims the benefit of priority from provisional application No. 60/077,659, filed Mar. 11, 1998.

FIELD OF THE INVENTION

The invention relates to a novel process of making liquid antacid calcium carbonate containing compositions for neutralizing stomach acid (and calcium source or calcium nutritional supplement) in humans and other animals.

BACKGROUND OF THE INVENTION

Liquid pharmaceutical compositions for delivery of an antacid are generally of the suspension form. They constitute a finely divided antacid active, in solid form which is suspended in a liquid medium. These compositions generally are alkaline, with typical pH values in the range of 7.5 to 8.7.

One problem faced by such liquid compositions is that the pH may drift either below or over the 7.5 to 8.7 pH limits due to equilibrium not being established within 24 hours between the carbonate salt and its environment. This results in such things as color changes if a pH sensitive dye is used, possible microbial growth, and acceleration of base catalyzed degradations.

One method which has been used to stabilize such a suspension is described in U.S. Pat. No 5,498,426, Wilson et al., which includes an alkali metal phosphate salt, and alkali metal bicarbonate salt in addition to the alkaline earth carbonate salt.

Another group of patents to Beyerle et al., U.S. Pat. No. 5,631,026 and U.S. Pat. No. 5,455,050 include with the calcium carbonate a magnesium carbonate and/or magnesium trisilcate as well as a carboxylic acid pH adjusting agent.

U.S. Pat. No. 5,002,777 discloses a concentrated suspension of calcium carbonate in a liquid carrier contained in a capsule, in which the liquid carrier is PEG 400.

The problem faced by the pH drift has not been successfully solved for liquid antacid compositions which are magnesium or aluminum free. The present invention is the recognition of this problem and a solution to such whereby a pleasant liquid antacid formulation is achieved which is pH stable.

SUMMARY OF THE INVENTION

The present invention is to a process of making an aluminum and magnesium free liquid antacid formulation which is stable at a pH from about 7.5 to about 8.7. The liquid antacid formulation is also free from antimicrobial contamination during the stable shelf life of the product.

The aluminum and magnesium free antacid formulation is a calcium carbonate aqueous antacid suspension having a pH of about 7.5 to about 8.7, which suspension is prepared by a process which comprises the steps of:

a) adding to water an effective amount of particulate calcium carbonate with mixing until the particulate is completely wetted and dispersed; and b) adding to said mixture of part a) with stirring an amount of a suspending agent for a time sufficient to substantially coat said particulate material, and to produce a suspension; or alternately adding b) to a) and;

c) while stirring, titrating the suspension of part b) with a pH adjusting agent to provide a pH of about 6.4 to 7.0 to the aqueous antacid suspension.

The present invention is also directed to a liquid antacid pharmaceutical formulation for neutralizing excess stomach acid. The present invention is also a method of orally administering to a mammal in need of such treatment an effective amount of said liquid antacid composition.

DETAILED DESCRIPTION OF THE INVENTION

The aqueous suspensions of the present invention have been found to be a stabilized liquid calcium carbonate containing antacid having a pH range of about 7.5 to about 8.7, meeting USP standards. The suspensions of this invention have been found to be stable with regard to antimicrobial, viscosity, defoaming, and acid neutralizing capacity (ANC) parameters, as well as to pH. The present invention has found that the selective order of addition and mixing of the essential components herein provides the stable pH of this suspension and further provides for the formation of a higher concentrated suspension of calcium carbonate than previously available to the marketplace. The higher dose formulation of liquid calcium carbonate, in addition to providing maximum acid neutralizing capacity, may also provide a 1000 mg of calcium per dosage to a mammal in need of such calcium for building bone, for treatment of osteoporosis, for pre-menstrual syndrome, etc.

The present invention is to an aqueous antacid suspension for oral use having a pH of about 7.5 to about 8.7 of calcium carbonate, prepared by a process which comprises:

a) adding to water an effective amount of calcium carbonate with mixing until the calcium carbonate is completely wetted and dispersed; and b) adding to said mixture of part a) with stirring a suspending agent for a time sufficient to substantially coat said carbonate, and to produce a suspension; alternatively, the suspending agent may be added to water first, and calcium carbonate adding second; and c) while stirring, titrating the suspension of part b) with a pH adjusting agent to provide a pH of about 6.4 to about 7.0 to the aqueous antacid suspension.

Suitable use of a thickening or suspending agents includes but is not limited to those generally used in aqueous antacid formulations, for example, microcrystalline cellulose, such as Avicel, xanthan gum, guar gum, methyl celluloses such as HPMC and sodium carboxymethylcellulose. Preferably, two suspending agents are used, Avicel and xanthan gum.

An appropriate wetting agent, such as glycerin may be utilized to insure maximum dispersion of the thickening agent in the aqueous system. To such end, the thickening agent, such as xanthan gum is preferably admixed with glycerin in a separate container prior to addition to the suspension/mixture. An alternative to the thickening agent/glycerin premix is the use of appropriate mechanical dispersing means, such as a high shear mixer to assist dispersion of the thickening agent. A commercially available readily dispersible thickening agents may also be used, such as KELTROL RD brand of readily dispersible xanthan gum from Kelco, division of Merck. Such readily dispersible thickening agents may provide adequate dispersion upon direct addition to the aqueous system.

Previous calcium carbonate liquid antacid suspensions have been found to be unstable, and have been found to have to high a resulting pH level. The pH level of the present invention is within the USP standards as has been found to be stable, and can be maintained with an efficient preservative system. Accordingly, a pH adjusting agent is a necessary component of the invention. Citric acid has been found to be a preferred pH adjusting agent, although other carboxylic acids such as tartaric, adipic, benzoic, carbonic, cinnamic, fumaric, glutaric, gluconic, hydroxybenzoic, malonic, malic, phthalic, oxalic, sorbic, succinic and the like may be utilized. The amount of pH adjusting agent should be sufficient to bring about, and maintain the pH of the final product in a range of 7.5 to about 8.7. In general from about 0. 025 to about 0.2% w/w of the pH adjusting agent has been found suitable. As the pH adjusting agent is added at the last step, while mixing, the titrate of the suspension with the pH adjusting agent will be added in an amount sufficient to provide a pH of about 6.4 to 7.0 of the aqueous antacid suspension. It is critical that the pH is measured within 15 minutes after the pH adjusting agent is added. The resulting suspension the next day should have equilibrated to the final desired pH range of from about 7.5 to about 8.7.

Any desired pharmaceutically acceptable adjuvant may be added. For examples, one or more preservatives, such as benzyl alcohol; flavouring agents, such as oil of orange, imitation wintergreen flavour, lemon-lime flavors, mint flavors, or combinations thereof; sorbitol serves to increase shelf life and palatability; wetting agents, an antiflatuent which is preferably simethicone, preferably in an antiflatuent amount of from about 0.1 to about 2.0% w/w is suitable; sweetening agents, such as calcium sacccharin; colouring agents; taste enhancing agents, such as calcium choride; and tetrapotassium pyrophosphate.

A unique aspect of the present invention is the order in which the essential buffering component must be admixed in order to the final suspension to achieve the desired pH range. If the pH adjusting agent is added to the active antacids prior to the last step, it tends to achieve a higher pH or an unstable suspension. It is therefore, critical that all of the components, but for the buffering, be added to the suspension and thoroughly dispersed with the gums prior to the addition of the pH adjusting agent.

A process which combines tetrapotassium pyrophosphate and citric Acid in one solution, at the same time, has a resulting pH which is inconsistent as it can either be below or over the 7.5 to 8.7 limit and takes about 30 days to equilibrate.

In a preferred embodiment, there are a number of separate phases of ingredients which are premixed prior to addition of the liquid antacid suspension. By this is meant, a calcium chloride phase, an first suspending agent phase, a second suspending agent phase, a sweetening phase, an the pH adjusting agent phase. Each individual component is admixed with a formula amount of water and held as a separate phase until addition to the preparation vessel.

While the order of addition to the preparation vessel is the preservative phase followed by the calcium chloride phase, either order is acceptable. To this mixture is added the first suspending agent, such as the Avicel premix, with continual mixing, until the batch becomes smooth and uniform, with no lumps. With continued mixing, the powdered calcium carbonate, USP is mixed. The suspension is stirred until the calcium carbonate is uniformly dispersed and thoroughly coated. To this suspension mixture is added, preferably while stirring is maintained, the second suspending agent, which is preferably xanthan gum. In a preferred aspect the xanthan gum is premixed, not with water but with glycerin. The resulting batch mixture is continued to be stirred until the xanthan gum is adequately hydrated.

To this batch mixture is added the sorbitol solution, USP admixed with formula amounts of water and continued stirring until the batch is uniform. If an antiflatulent, or any other suitable biologically active agents are desired to be added to the suspension, they are added at this stage until the batch is uniform.

While continued mixing, the sweetening phase is added and with continued stirring until uniform. While mixing the optional flavouring agents are also added. Again, the order of addition of these excipients is variable, and may be added at any step herein, a preferred embodiment being in this explicit order. At this time, it is preferred that a batch pH be taken. To this admixture is added the buffering agent phase with an additional formula water. The batch is slowly mixed until uniform. A batch pH is again (or first taken) at this step in the process. To this batch, the pH adjusting phase is now titrated. The Citric Acid Phase is titrated to a target pH of about 6.4 to 7.0. The pH is measured within 15 minutes after the pH adjusting agent is added.

As a guideline, the citric acid phase (CAP) is administered in accordance with the batch pH of the mixture prior to addition of the CAP. If the batch pH before CAP titration is equal to or greater than 7.5, approximately 0.2625% w/w CAP (equivalent to 0.075% w/w Citric Acid) is added, and if necessary more CAP is added in 0.0875% w/w increments (equivalent to 0.025% w/w Citric Acid), until the target pH is reached. The batch is mixed until uniform, or approximately 15 minutes. The pH is measured within 15 minutes after each increment.

If the batch pH before CAP titration is equal to or less than 7.5, approximately 0.0875% w/w CAP (equivalent to 0.025% w/w Citric Acid) is added, and if necessary more CAP is added in increments of 0.0875% w/w CAP until the target pH is reached. The batch is mixed until uniform, or approximately 15 minutes. The pH is measured after each increment.

While not dispositive of the effects of calcium carbonate solubility as it applies to the pH problem for stabilization of liquid antacid suspensions, the following has been observed:

That the reactions associated with calcium carbonate solubility in water are a combination of:

$$CaC(O)_3(solid) \leftrightarrows Hydration \leftrightarrows CaC(O)_3(hydrate) + H_2O +$$
$$C(O)_2 \leftrightarrows Ca(HCO_3)_2 \leftrightarrows Ca^{++} + HCO_3^-$$

$$CaC(O)_3(hydrate) \leftrightarrows Ca^{++} + CO_3^-$$

$$H_2O + C(O)_2 \leftrightarrows H_3O^+ + HCO_3^-$$

The hydration step is the rate limiting step for dissolution.

The solubility of calcium carbonate is about 0.05–0.07% mg/ml at room temperature. The pH of a 10% dispersion of calcium carbonate in water (saturated solution) is about 9.0.

The solubility of calcium carbonate is increased by an increase in carbon dioxide solubilized in the water. The solubility of calcium carbonate decreases with increasing temperatures. The rate of agitation influences the rate of solubility of calcium carbonate. It could take up to 5 days for the saturated solution of calcium carbonate in water to be formed. It takes less than one day if air (carbon dioxide) is passed through the mixture prior to stirring.

Phosphates and anionic surfactants sequester calcium increasing both the rate and extent of solubilization of calcium carbonate. However, some phosphates adhere to the calcium carbonate particle surface inhibiting the sequestration.

Based upon this information, and the assumption that the pH change in the calcium carbonate liquid suspension is due solely to the rate of solubilization of calcium carbonate, the CAP should be added after the saturated solution of calcium carbonate is formed. The emulsifier/texturizer with buffering properties, in this case, tetrapotassium pyrophosphate, could be added first with time need to reach a constant pH. Once the constant pH is reached after the phosphate addition, the pH adjusting agent, CAP, could be added to adjust the pH to a lower USP limit.

Another aspect of the present invention is a stable, high dosage calcium carbonate aqueous antacid formulation which comprises:

| | |
|---|---|
| Avicel NF | 0.52 |
| Calcium Carbonate, USP | 17.47 |
| Glycerin, NF | 5.00 |
| Xanthan Gum, NF | 0.28 |
| Sorbitol, USP | 10.00 |
| Citric Acid Anhydrous, USP* | 0.025 to 0.20 |
| Water, USP | qs 100% w/w |

Another aspect of the present invention is the stable, high dosage calcium carbonate and simethicone containing aqueous antacid formulation which comprises:

| | |
|---|---|
| Avicel NF | 0.52% w/w |
| Calcium Carbonate, USP | 17.47 |
| Glycerin, NF | 5.00 |
| Xanthan Gum, NF | 0.28 |
| Sorbitol, USP | 10.00 |
| Simethicone, USP, 30% | 1.75 |
| Flavouring agent | 1.05 |
| Citric Acid Anhydrous, USP* | 0.20 |
| Water, USP | q.s. 100 |

Another aspect of the present invention is a method for neutralizing excess stomach acid in a mammal in need thereof, which method comprises orally administering to said mammal an effective amount of a liquid antacid suspension as noted above.

The invention will now be described by reference to the following examples which are merely illustrative and are not to be construed as a limitation of the scope of the present invention.

EXAMPLE 1

The following phases are prepared, not necessarily in the following order. Each phase may be prepared concurrent with or immediately before adding to the main batch in the preparation vessel.

The xanthan gum phase is prepared by dispersing the gum in glycerin. The Avicel gum is prepared by dispersing in water. The calcium chloride phase, the calcium saccharin phase, the tetrapotassium pyrophosphate phase, and the citric acid phase are prepared by dissolving each phase component in water.

The main batch is prepared by charging water into the Mixing Tank, followed by the addition of Benzyl Alcohol, Calcium Chloride Phase, Avicel Gum Phase, Calcium Carbonate, Xanthan Gum Phase, Simethicone, Calcium Saccharin Phase, Flavouring Agent(s), and optionally the Tetrapotassium Pyrophosphate phase. The addition to the main batch may be in any order provided that the batch is uniform, dispersed and the calcium carbonate well coated, prior to the addition of the CAP phase. The batch pH is adjusted to a target of about 6.4 using the CAP. The final batch pH is measured after one day.

| INGREDIENTS | AMOUNTS % W/W |
|---|---|
| Water, USP | 65.34 |
| Benzyl Alcohol, NF | 0.75 |
| Calcium Chloride, USP | 0.12 |
| Avicel NF | 0.52 |
| Calcium Carbonate, USP | 17.47 |
| Glycerin, NF | 5.00 |
| Xanthan Gum, NF | 0.28 |
| Sorbitol, USP | 10.00 |
| Calcium Saccharin, USP | 0.10 |
| Flavour(s) | 1.43 |
| Tetrapotassium Pyrophosphate, FCC | 0.08 |
| Citric Acid Anhydrous, USP* | 0.200 |

*Actual amount used can vary between 0.025 and 0.20 w/w depending upon titration pH. The citric acid USP in the formula is used to adjust the batch pH to a target pH of about 6.4 to 7.0.

Each 5 ml contains 1000 mg Calcium Carbonate.

The Calcium Chloride Phase is made by admixing, Water, USP 1.00% w/w and Calcium Chloride 0.12% w/w.

The Avicel Gum Phase is made by admixing Water, USP 21.00% w/w and Avicel 0.52% w/w.

The Xanthan Gum Phase is made by admixing Glycerin, NF 4.50% w/w and Xanthan Gum, 0.28% w/w.

The Calcium Saccharin Phase is made by admixing Water, USP, 1.0% w/w and Calcium saccharin 0.10% w/w.

The Tetrapotassium Pyrophosphate Phase is made by admixing Water, USP 1.00% w/w and tetrapotasium pyrophosphate, FCC 0.080% w/w.

The Citric Acid Phase is made by admixing Water, USP 0.50% w/w to Citric acid USP 0.20% w/w.

EXAMPLE 2

As above, the phases are prepared, not necessarily in a particular order. Each phase may be prepared concurrent with or immediately before adding to the main batch in the preparation vessel.

Also, as above, the addition to the main batch may be in any order of each of the components, provided that the batch is uniform, dispersed and the calcium carbonate well coated, prior to the addition of the CAP phase. The batch pH is adjusted to a target of about 6.4 to 7.0 using the CAP. The final batch pH is measured after one day.

| INGREDIENTS | AMOUNTS % W/W |
|---|---|
| Water, USP | 63.63 |
| Benzyl Alcohol, NF | 0.75 |
| Calcium Chloride, USP | 0.12 |
| Avicel NF | 0.52 |
| Calcium Carbonate, USP | 17.47 |
| Glycerin, NF | 5.00 |
| Xanthan Gum, NF | 0.28 |
| Sorbitol, USP | 10.00 |
| Calcium Saccharin, USP | 0.10 |
| Simethicone, USP, 30% | 1.75 |
| Flavour | 1.05 |
| Tetrapotassium Pyrophosphate, FCC | 0.08 |
| Citric Acid Anhydrous, USP* | 0.20 |

*Actual amount used can vary between 0.025 and 0.20 w/w depending upon titration pH. The citric acid USP in the formula is used to adjust the batch pH to a target pH of about 6.4 to 7.0.

Each 5 ml contains 1000mg Calcium Carbonate and 30 mg Simethicone

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method for neutrallizing excess stomach acid in a mammal in need thereof, which method comprises orally administering to said mammal an effective amount of a liquid antacid suspension having a formula comprising:

| | |
|---|---|
| Avicel NF | 0.52 |
| Calcium Carbonate, USP | 17.47 |
| Glycerin, NF | 5.00 |
| Xanthan Gum, NF | 0.28 |
| Sorbitol, USP | 10.00 |
| Citric Acid Anhydrous, USP | 0.025 to 0.20 |
| Water, USP | q.s. 100% w/w. |

2. A method for neutralizing excess stomach acid in a mammal in need thereof, which method comprises orally administering to said mammal an effective amount of a liquid antacid sispension of the formula comprising:

| | |
|---|---|
| Avicel NF | 0.52 |
| Calcium Carbonate, USP | 17.47 |
| Glycerin, NF | 5.00 |
| Xanthan Gum, NF | 0.28 |
| Sorbitol, USP | 10.00 |
| Simethicone, USP, 30% | 1.75 |
| Flavouring agent | 1.05 |
| Citric Acid Anhydrous, USP | 0.20 |
| Water, USP | q.s. 100% w/w. |

3. A method of preparing a stable aqueous antacid suspension for oral use with a pH of about 7.5 to about 8.7 which comprises:

a) adding to water an effective amount of calcium carbonate with mixing until the calcium carbonate is completely wetted and dispersed; and b) adding to said mixture of part a) with stirring a suspending agent for a time sufficient to substantially coat said calcium carbonate, and to produce a suspension; or alternately adding b) to a);

c) while stirring, titrating the suspension of part b) with a pH adjusting agent to provide a pH of about 6.4 to 7.0 to the aqueous antacid suspension; and d) upon standing the suspension will equilibrate to a stable pH of about 7.5 to 8.7.

4. The suspension according to claim 3 wherein the suspending agent of part b) is first added to water prior to the addition of the calcium carbonate.

5. The suspension according to claim 4 wherein the suspending agent is comprised of two different agents, and the first suspending agent is microcrystalline cellulose.

6. The suspension according to claim 5 wherein the second suspending agent is xanthan gum.

7. The suspension according to claim 6 wherein the xanthan gum is admixed with glycerin prior to adding to the suspension.

8. The suspension according to claim 3 wherein the pH adjusting agent is citric acid.

9. The suspension according to claim 8 wherein the citric acid in water is titrated to the suspension of part (b) on the basis of batch testing of the suspension wherein the batch pH is greater or less than a pH of 7.5.

10. The method according to claim 3 which further comprises the addition of a flavouring agent to the suspension.

11. The method according to claim 3 which further comprises the addition of an effective amount of an antiflatuent which is simethicone to the suspension.

12. The method according to claim 3 which further comprises the addition of both sorbital and a sweetening agent to the suspension.

13. The method according to claim 3 which further comprises the addition of tetrapotassium pyrophosphate to the suspension.

14. The method according to claim 3 wherein the calcium carbonate is from about 1.5 to about 20.0% w/w.

* * * * *

UNITED STATES PATENT AND TRADEMARK OFFICE
CERTIFICATE OF CORRECTION

PATENT NO. : 6,368,638 B1  Page 1 of 1
DATED : April 9, 2002
INVENTOR(S) : Antonio Tiongson It is certified that error appears in the above-identified patent and that said Letters Patent is hereby corrected as shown below:

Column 8,
Lines 12 and 15, replace "suspension" with -- method --.
Lines 19 and 21, replace "suspension" with -- method --.
Lines 24 and 27, replace "suspension" with -- method --.

Signed and Sealed this

Twenty-ninth Day of April, 2003

JAMES E. ROGAN
*Director of the United States Patent and Trademark Office*